United States Patent [19]

Atake

[11] Patent Number: 4,728,501

[45] Date of Patent: Mar. 1, 1988

[54] ADJUSTABLE LIQUID SAMPLING APPARATUS

[76] Inventor: Minoru Atake, 579-6, Ohoiso, Ohoiso-macchi, Naka-gun, Kanagawa-ken, Japan

[21] Appl. No.: 675,350

[22] Filed: Nov. 27, 1984

[30] Foreign Application Priority Data

Jul. 27, 1984 [JP] Japan .................................. 59-157868
Jul. 27, 1984 [JP] Japan .................................. 59-157869

[51] Int. Cl.$^4$ .......................... B01L 3/02; G01F 1/20; G01N 1/14
[52] U.S. Cl. ................................. 422/100; 73/863.32; 73/864.18
[58] Field of Search ............................ 422/100, 63, 65; 73/863.32, 864.01, 864.18

[56] References Cited

U.S. PATENT DOCUMENTS

| 3,141,336 | 7/1964 | Oates | 422/100 |
| 3,737,501 | 6/1973 | Dunipace | 264/159 |
| 4,325,909 | 4/1982 | Coulter et al. | 422/100 |
| 4,434,672 | 3/1984 | Williamson et al. | 422/100 |
| 4,478,094 | 10/1984 | Salomas et al. | 422/100 |
| 4,528,161 | 7/1985 | Eckert | 422/100 |
| 4,609,017 | 9/1986 | Coulter et al. | 422/100 |

FOREIGN PATENT DOCUMENTS

| 8404056 | 10/1984 | European Pat. Off. | 422/100 |
| 2447751 | 1/1979 | France |

Primary Examiner—S. Leon Bashore
Assistant Examiner—Michael K. Boyer
Attorney, Agent, or Firm—Frishauf, Holtz, Goodman & Woodward

[57] ABSTRACT

A liquid sampling apparatus for adjusting the amount of sampled fluid drawn into a cylinder. A carriage reciprocates vertically and drives a rod inclined at an acute angle to the vertical direction. The axes of the cylinder and the rod are parallel to each other. Motion of the rod moves a piston in the cylinder to sample the fluid. A push member rotatably coupled to the carriage can be adjusted at an angle to the horizontal direction. Because the push member engages the rod to drive it during carriage motion, a given stroke of the carriage produces varying travel distances of the rod depending on the angle to which the push member is set.

4 Claims, 20 Drawing Figures

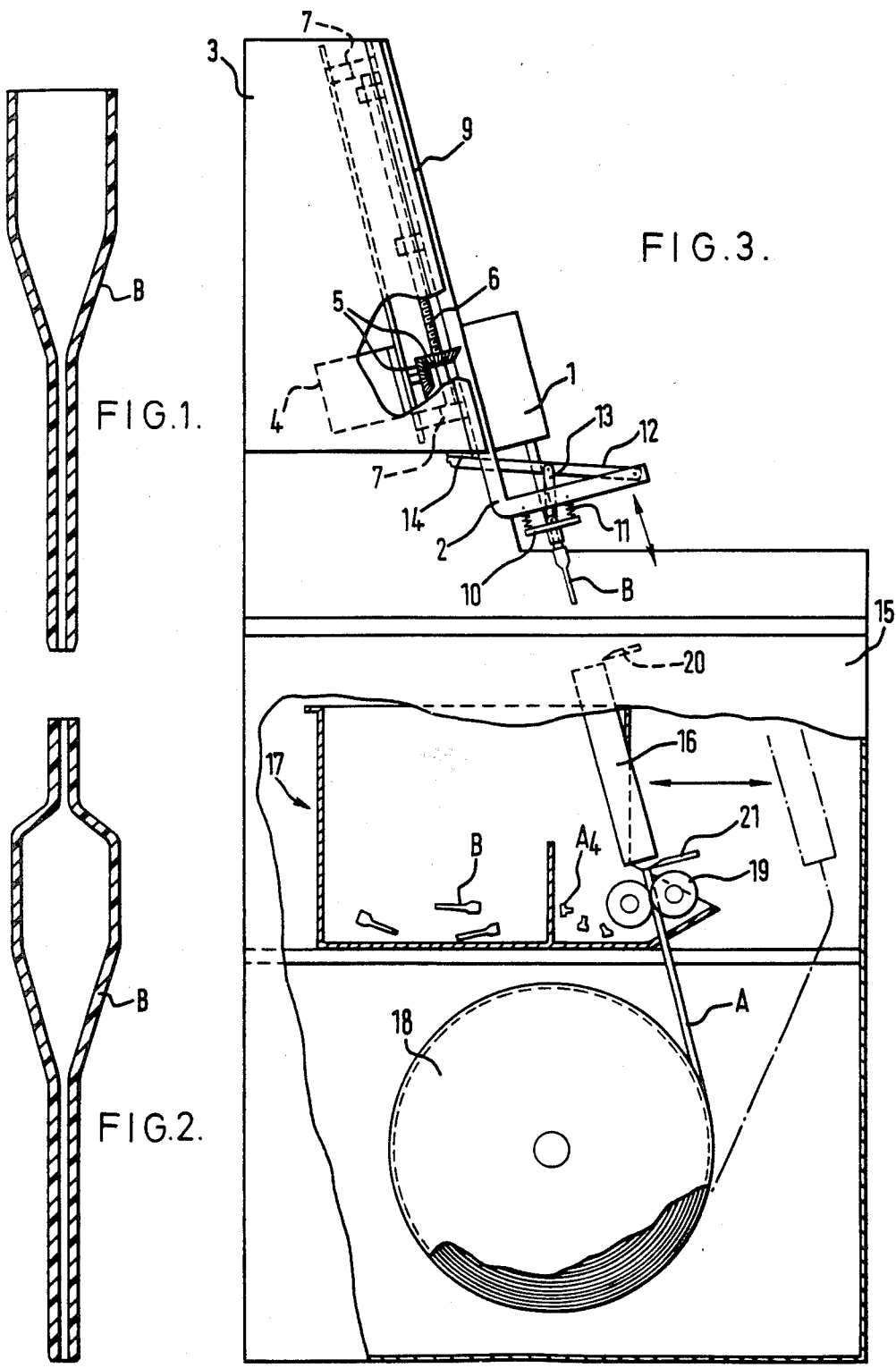

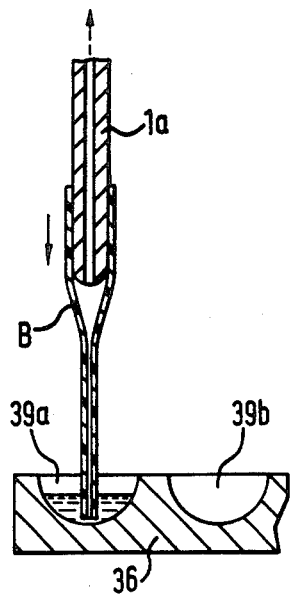
FIG.8a.
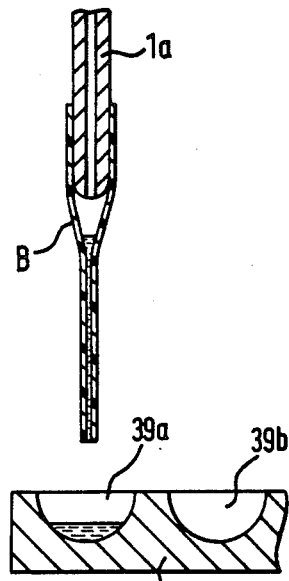
FIG.8b.
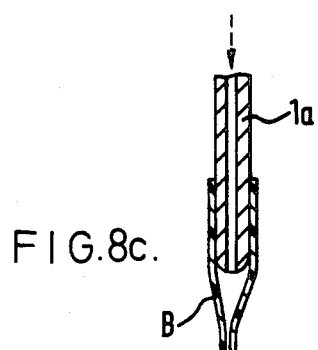
FIG.8c.
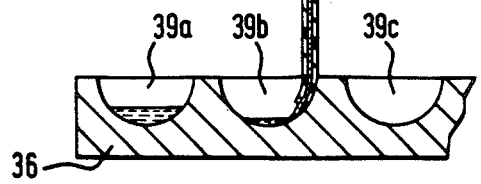

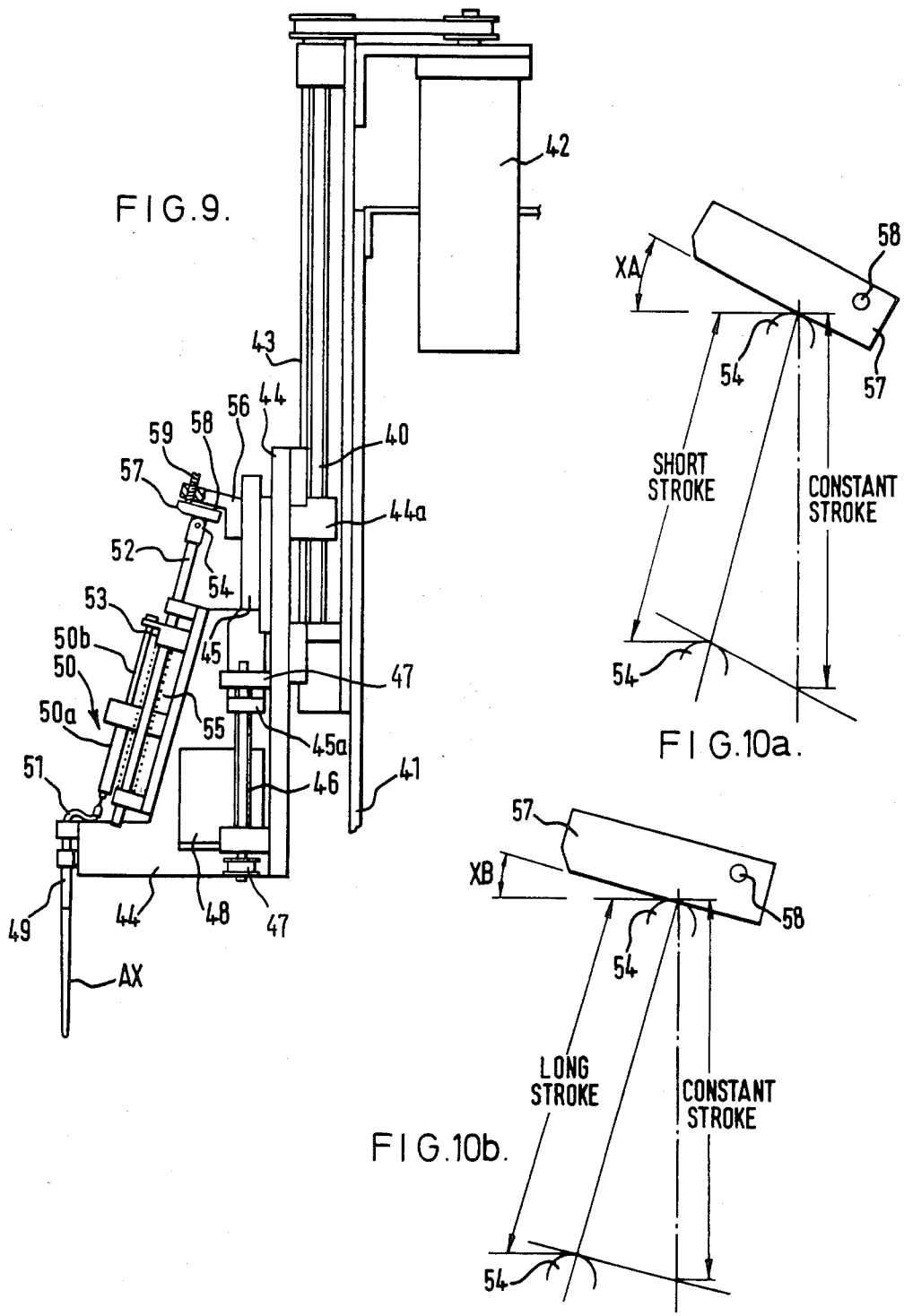

4,728,501

ADJUSTABLE LIQUID SAMPLING APPARATUS

BACKGROUND OF THE INVENTION

This invention is directed to a technique for aspirating and expelling sample fluids of a test material and, more particularly, to an apparatus including micro-pipettes which can be adjusted as to the amount of the sample accommodated therein.

Laboratory analysis apparatus includes equipment for processing fluids, such as blood, to be analyzed. The fluid is contained in a holder such as a test tube. Only a predetermined amount of the test material must be removed. Equipment exists for reaching the test material with a probe such as a micro-pipette ("pipette" hereafter). A pipette has a cylindrical body with a long nose of small diameter. A piston in the body is moved by a rod to aspirate fluid into it or expel fluid from it. The extent to which the piston moves determines the amount of fluid sampled.

A conventional technique for controlling the amount of fluid sampled couples the rod to a stepper motor. The rotation of the motor can be accurately controlled. Such rotation is translated into axial motion of the rod by a suitable motion conversion mechanism. A large number of such samples can be taken simultaneously by putting the pipettes on a rack. The rod of each pipette is also connected to a rack which is moved by a motor. As the rack moves, all the samples are taken simultaneously.

An approach such as that described just above has several disadvantages. A relatively sophisticated and, therefore, expensive motor must be used to precisely and adjustably vary the motion of the rod. Also, the control circuitry for setting and adjusting the motor rotation is also sophisticated and expensive. Individual adjustment of a pipette relative to the other pipettes on the rack is not possible. Individual setting of this sort requires a dedicated motor for each pipette.

SUMMARY OF THE INVENTION

One object of the invention is to provide a liquid sampling apparatus that is accurate yet relatively simple and inexpensive.

Another object of the invention is to provide a liquid sampling apparatus that utilizes a plurality of pipettes which can be individually adjusted as to the amount of fluid sampled.

A further object of the invention is to provide a liquid sampling apparatus that utilizes a plurality of pipettes which can be individually adjusted as to the amount of fluid sampled.

These and other objects of the invention are attained by a liquid sampling apparatus for drawing and/or expelling a test liquid of a predetermined amount into a hollow cylinder, comprising: a support, a vertically movable carriage, motive means mounted on the support to reciprocally move the carriage by a predetermined distance in a vertical direction relative to the support, a hollow cylinder fixed to the support with its axis inclined at an acute angle to the vertical direction, a piston means movable in the cylinder to draw a liquid sample into or expel it from the cylinder, a rod having one end coupled to the piston means, the axis of the rod being parallel to the axis of the cylinder, a push member mounted on the carriage and positioned to engage the other end of the rod as the carriage is reciprocated vertically, the push member extending in a generally horizontal direction, and adjustment means for pivoting the push member to vary an angle between the push member and the horizontal direction.

BRIEF DESCRIPTION OF THE DRAWINGS

FIG. 1 is a longitudinal cross-section of a micro-pipette embodying this invention;

FIG. 2 is a longitudinal cross-section of another embodiment of a micro-pipette according to the invention;

FIG. 3 is a partly broken away side view of a device for manufacturing such micro-pipettes;

FIGS. 8(a) to 8(c) show successive steps for sampling the test material by micro-pipettes immediately after fabrication;

FIG. 9 is a side view of a device for subdividing test material by a plurality of micro-pipettes; and FIGS. 10(a) and 10(b) show an operation of the essential part of the device of FIG. 9.

BRIEF DESCRIPTION OF THE PREFERRED EMBODIMENTS

Figure 4:
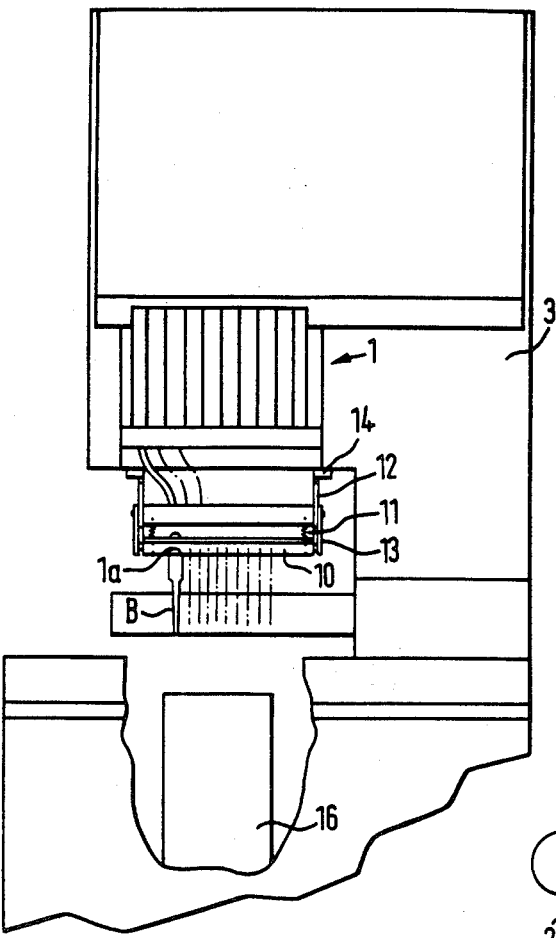
FIG. 4 is a front view of part of the device of FIG. 3.

In the drawings, a head block 1 has a plurality of attaching rods 1a to which synthetic polymer tubes A are removably attached with their forward ends set onto rods 1a. The head block 1 is supported on a holder 2 mounted on a frame 3 in a manner to move reciprocally in a vertical direction. A reversible motor 4 attached to the frame 3 drives, via bevel gears 5, a screw shaft. The screw shaft 6 is rotatably supported to bearings 7 attached by the holder 2 in a manner to vertically guide the holder 2 along rails 9 disposed on the frame 3.

A stripper plate 10 is suspended beneath the holder 2 by means of spring members 11 and pivotably connected to a link 13, which is in turn pivoted to a lever 12 itself pivoted to the front end of the holder 2. A stopper 14 is attached to the frame 3 so as to limit the motion of the lever 12 upwards. The stripper plate 10 has a plurality of guide holes through each of which one of the attaching rods 1a is slidably moved respectively.

A base frame 15 for supporting the frame 3 has an inner space in which a pipette forming device 16 and a receiver 17 are disposed in a manner to be forwardly movable together (means for moving the device 16 and receiver 17 is not shown in the drawing). Reels 18 stock a wound supply of tubes A, each reel being suitably located relative to a corresponding attaching rod 1a and isposed under the device 16 and receiver 17.

In this embodiment, the tube A may be made from thermal shrinkable synthetic polymer and guided to the forming device 16 by means of feed rollers 19, which are driven by means of a reversible motor (not shown) and stopped by means of brake members (not shown). At upper and lower ends of the forming device 16 are disposed cutters 20 and 21.

Figure 5:
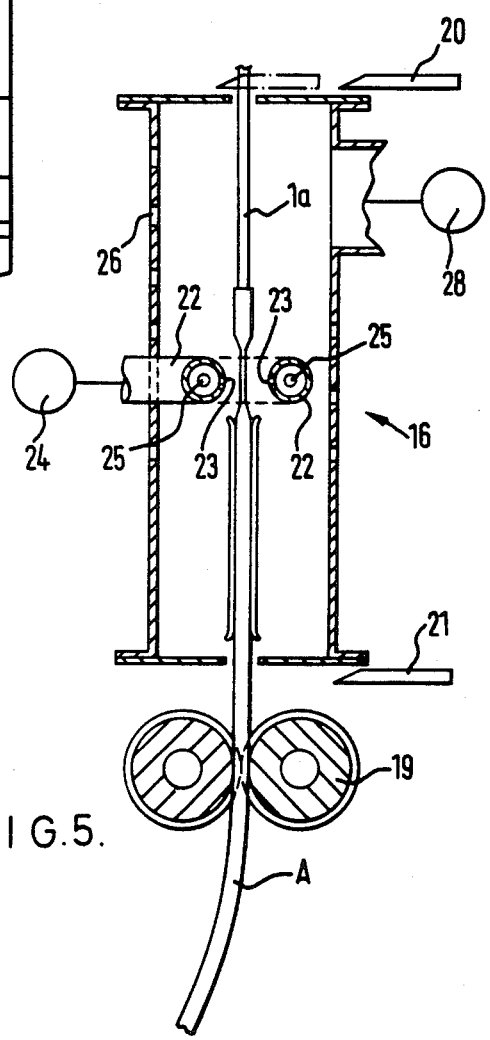
FIG. 5 shows means for heating a tube of synthetic resin and which is part of the device of FIGS. 3 and 4.
Figure 6A:
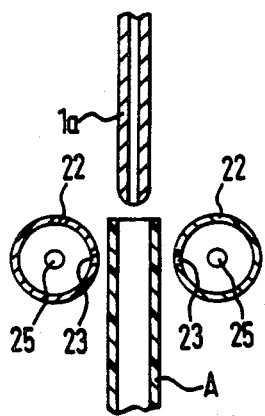
FIG. 6(a) to (h) indicate the successive steps for manufacturing the micro-pipette shown in FIGS. 1 and 2.
Figure 6B:
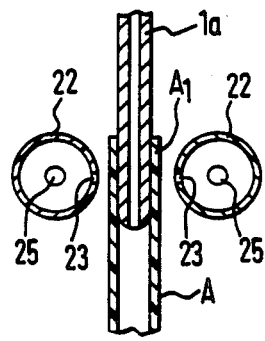
Figure 6C:
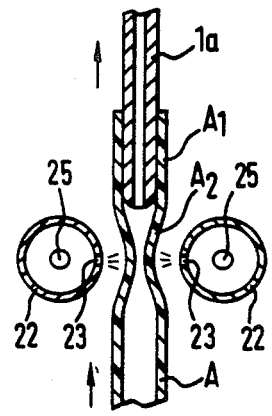
Figure 6D:
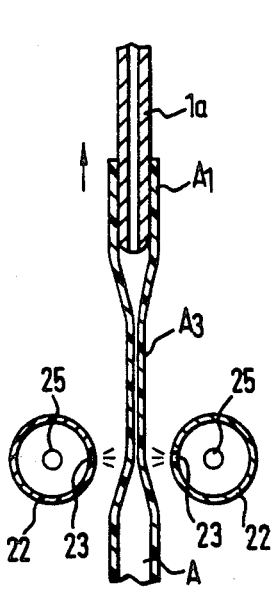
Figure 6E:
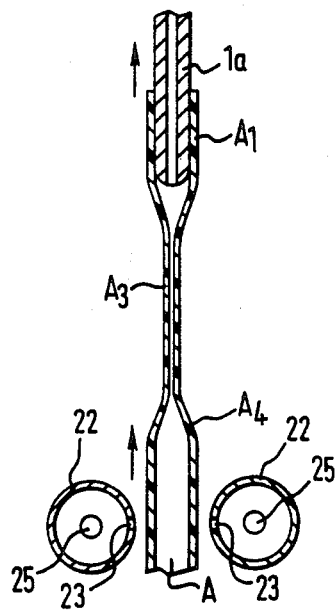
Figure 6F:
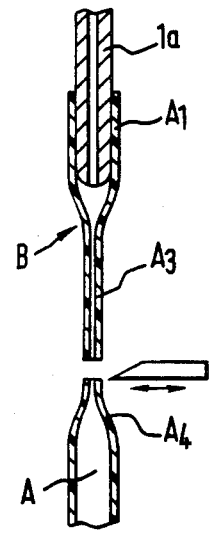
Figure 6G:
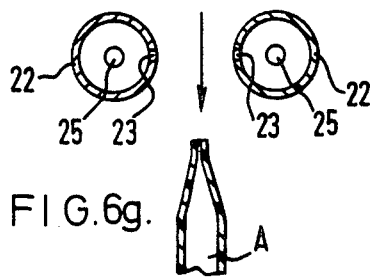
Figure 6H:
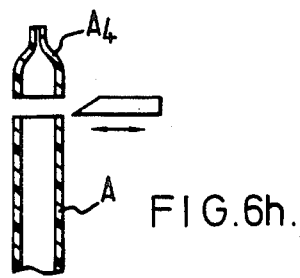

The pipette forming device 16 (FIG. 5) comprises heat tubes 22 parallel to and spaced from each other. Each of these tubes has a plurality of through bores 23 facing the other heat tube. The tubes are connected to a blower 24 and heated by meas of heaters 25 disposed in each of the heat tubes 22. Hot air is blown out from the through bores 23 toward the both sides of each of supplied tubes A lying parallel to each other and extending upwards in the shell of the pipette forming device 16.

In operation, the motor 4 drives the bevel gears 5 to cause the holder 2 to be moved downwards and to insert the lower ends of the attaching rods 1a into the upper opening of the forming device 16. They enter the respective upper ends of tubes A as the tubes A are supported by the feed rollers 19. The slight rotation of the feed rollers 19 results in shifting the upper ends of tubes A upwards so as to set each firmly on the attaching rod 1a. Simultaneously, the motor 4 is reversed and slightly drives in reverse direction so that the attaching rods 1a are moved upwards together with the tubes A. Then, the blower 24 acts to cause the heated air to be blown on the outside of tubes A so that the upper portions A1 of the tubes A are shrunk by air-heating and fixed to the attaching rods 1a.

Thereafter, the feed rollers 19 moves to supply the tubes A upwards and the attaching rods 1a are upwardly moved by the motor 4 under a speed higher than that of the tube supply.

Accordingly, the portion A2 positioned to the portion A1 is shrunk by air-heating and simultaneously stretched in a lengthwise. Thereafter, the feed rollers 19 is stopped by brake members (not shown), and the motor 4 drives continuously so as to move the attaching rods 1a together with tubes A, until long "noses" A3 are formed respectively with a prescribed inner diameter small and uniform throughout its length.

Thereafter, the blower 24 is stopped, the heater 25 is de-energized, the vacuum pump 28 pulls air through bores 26 in the shell and into the pipette-forming device and thereby cooling the portion A3.

Then, the feed rollers 19 are driven again by the same speed as that of the attaching rods 1a so as to supply the tube A upwards. When the portion A3 emerges from the forming device 16, the attaching rods 1a and feed rollers 19 are stopped and then the portions A3 are cut off from the bodies of the tubes A by means of cutter 20.

Next, the motor 4 drives again in the reverse direction so as to move the attaching rods 1a up to a setting level. During such motion of the attaching rods 1a, the feed roller 19 is driven in reverse until the remaining portion A4 of the tube A is pulled back almost to the bottom opening of the pipette-forming device 16. When the feed roller 19 is stopped, the remaining portions A4 are cut off from the bodies of the tubes A by knife 21 and drop down to the receiver 17. At this stage, the vacuum pump 28 is stopped. Then, the pipette-forming device 16 and pipette-receiver 17 are jointly horizontally moved and a separate portion 17a formed in the receiver 17 is positioned under micro-pipettes B still attached to the attaching rods 1a.

The sequence of steps described above are illustrated in FIG. 6(a) to (h).

When the holder 2 moves upwards when driven by motor 4, the free end of the lever 12 is prevented from being moved upwards by the stop 14. This causes the stripper plate 10 to be moved downwards so as to slip the micro-pipettes B off attaching rods 1a toward the portion 17a.

The micro-pipettes B are produced one by one with operating steps mentioned above. This micro-pipette has a long "nose" with small inner diameter uniform along its length, for example, 0.3–0.7 mm, thereby to exhibit a long visible measuring display even with only a slight amount of test material in the long "nose" of the pipette.

Figure 7:
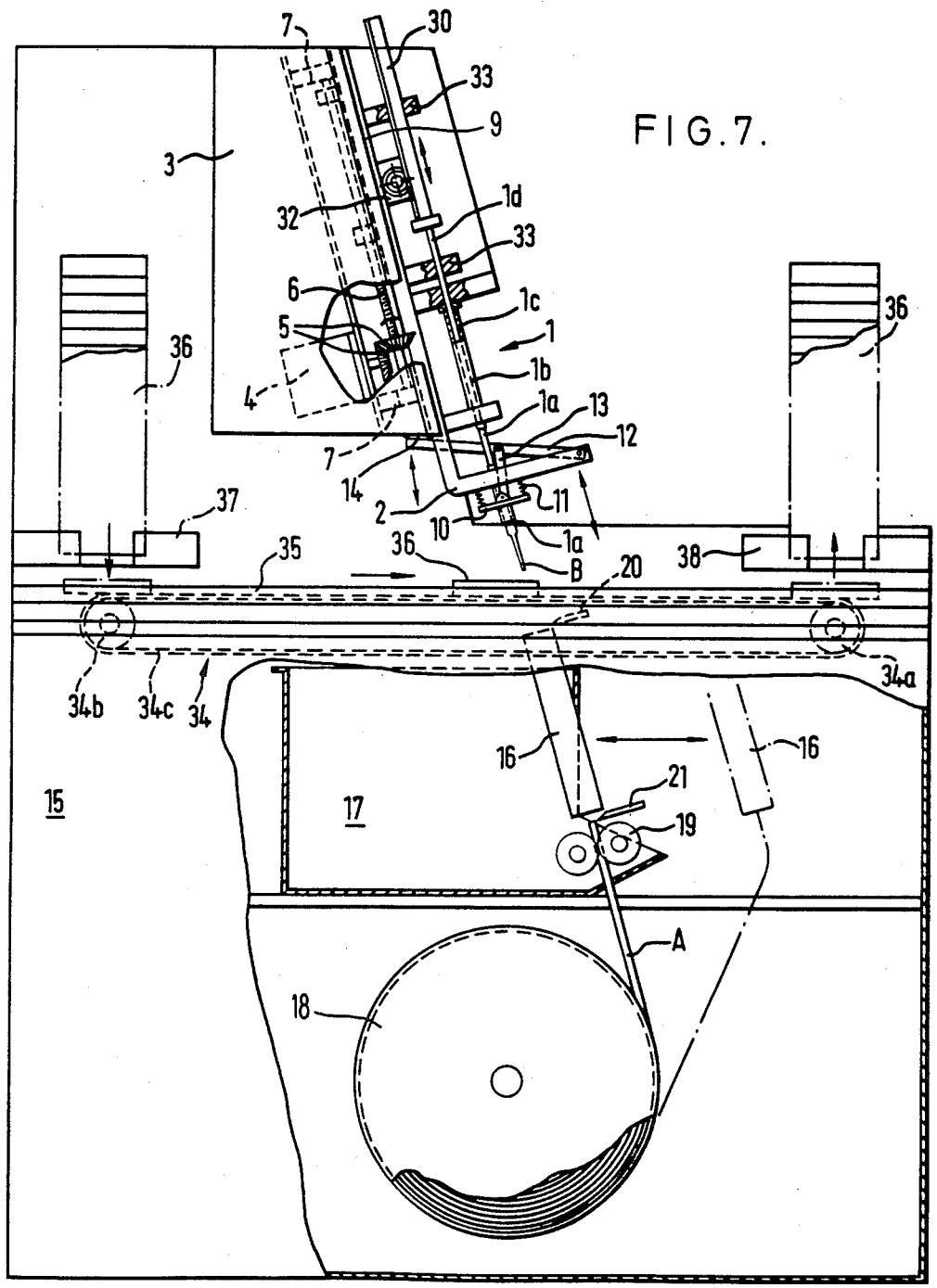
FIG. 7 is a partly broken away side view of a device for manufacturing micro-pipettes in use as a stage for sampling test material pipettes into a plurality of test tubes as another embodiment.

The second embodiment includes a device for subdividing test material such as sera. In this case, as shown in FIG. 7, the head block 1 comprises a plurality of hollow cylinders 1b each connected to one of the attaching rods 1a. The cylinders 1b have pistons 1d therein, respectively, connected to a rack member 30. The rack teeth are engaged with a pinion gear 31 which is driven by means of a motor 32 attached to the frame 3. The pistons 1d and rack member 30 are jointly slidably supported in bearings 33 mounted on the holder 2. On the base frame 15 is provided a belt conveyer 34 with a pair of endless belts 34a stretched between wheels 34b and 34c positioned to the front and rear portions of the base frame 15. Along the upper side portions of the endless belts 34a, a pair of parallel guide rails 35 are disposed so as to guide a stocker 36 as it is moved by the conveyer 34 from rear portion of the base frame 15 to a sampling position under the head block 1, and from the sampling position to the front portion of the base frame 15.

Means 37 for feeding the stocker 36 to the conveyer 34, and means 38 for accumulating the stockers 36 one by one are provided to the front and rear portions of the base frame 15.

In operation, before being slipped off by means of the stripper plate 10, the micro-pipettes B are moved downwards by driving the motor 4 when one of the stockers 36 arrives under the head block 1. The pipettes are, thus, inserted into sample containers 39a formed on the stocker 36. Thereafter, by driving the motor 32, the rack member 30 is shifted up so as to aspirate the test material into cylinders 1b as shown in FIG. 8(a).

Then, the micro-pipettes B are jointly lifted by driving the motor 4 in reverse as shown in FIG. 8(b). By driving the conveyer 34, the stocker 36 is transferred step by step with a prescribed pitch. The pipettes B are jointly shifted down by driving the motor 4 so as to be inserted into the next sample containers 39b aligned in a transferring direction as shown in FIG. 8(c). The motor 32 and rack 30 are moved to expel the fluid in the pipette.

In order to aspirate the test material into the plurality of pipettes simultaneously and to ensure that they aspirate amounts exactly equal to each other, there is provided a device for attachment to the above for dividing the test material exactly from the pipettes to the corresponding receivers as shown in FIG. 9.

The device comprises a screw-threaded shaft 40 vertically extended and rotatably supported on a frame 41 and rotatable by means of driving motor 42. Guide rails 43 are disposed parallel to the shaft 40. A carriage 44 is movable relative to the frame 41 in a vertical direction along the length of the rails 43 because its holder 44a engages the shaft 40. A sub-carriage 45 is also movable relative to the carriage 44 in a vertical direction with its holder 45a turnably engaging a screw-threaded shaft 46 supported in bearings 47 attached to the carriage 44 and rotatable by driving motor 48 disposed o the carriage 44.

On the carriage 44 are disposed a plurality of attaching rods 49 arranged in parallel to each other so as to be used for holding corresponding pipettes Ax, and piston cylinder assemblies 50 are coupled to the attaching rods 49 respectively.

Each of the piston cylinder assemblies 50 includes a hollow cylinder 50a supported on the carriage 44, and a piston 50b slidably inserted into the cylinder 50a. A path (not shown) formed to the inner portion of the attaching rod 49 is communicated with the inner chamber of the cylinder 50a through a flexible tube 51.

The device further comprises a guide rod 52 arranged in parallel to the piston 50b and engaged therewith by means of an engaging member 53. A contact roller 54 is provided at the top end of the guide rod 52, and a spring member 55 surrounds each guide rod to bias the engaging member 53 upwards. The guide rods 52 together with the pistons 50b are slidably supported in a direction inclined to that of the movement of the carriage 44 by a prescribed angle. The sub-carriage 45 includes an adjuster plate 56 attached to the front and top of the sub-carriage 45. Push members 57 corresponding one to each of the guide rods 52 are pivoted to the adjuster plate 56 by means of pins 58 so as to push the contact rollers 54 individually in dependence upon the setting of adjusting screws 59 threaded through the adjuster plate 56 so that the push members 57 are individually adjusted.

The relation between the inclinations of push members 57 and piston strokes of the piston cylinder assemblies 50 when the sub-carriage 45 is vertically moved by the motor driving motion, is illustrated by two examples of FIG. 10(a) and 10(b). The example shown in FIG. 10(a) has a small piston stroke for a constant stroke L of the subcarriage 45 when one of the push members 57 is adjusted with a large angle XA. The example shown in FIG. 10(b) has a large piston stroke for the same stroke L of the sub-carriage 45 since its push member 57 is adjusted with a small angle XB.

Accordingly, when many piston cylinder assemblies 50, the corresponding attaching rods 49 and pipettes Ax are used simultaneously to divide the test material into many receivers in exactness, the individual adjusting operation enabled by readily accessible screws 59 is very important and effective.

What is claimed is:

1. A liquid sampling apparatus for drawing and/or expelling a test liquid of a predetermined amount into a hollow cylinder, comprising:
   a support;
   a vertically movable carriage;
   motive means mounted on said support to reciprocally move said carriage by a predetermined distance in a vertical direction relative to said support, wherein the motive means comprises a motor;
   a hollow cylinder fixed to said support with a longitudinal axis of said hollow cylinder being inclined at an acute angle to said vertical direction;
   a piston means movable in said cylinder to draw a liquid sample into or expel it from said cylinder;
   a rod having one end coupled to said piston means, the axis of said rod being parallel to the axis of said cylinder;
   a push member mounted on said carriage and positioned to engage the other end of said rod as said carriage is reciprocated vertically, said push member extending in a generally horizontal direction, wherein the push member and the other end of said rod are in abuttment with each other as the carriage is moved downward;
   adjustment means for pivoting said push member to vary an angle between said push member and the horizontal direction, and wherein said adjustment means comprises a plate connected at one end of the carriage and extending therefrom at a generally horizontal direction, a pivot rod connected at said one end of the plate and accommodated in a means defining an opening of said push member located at one end thereof, and a setting means at the other end of said plate for vertically moving the other end of said push member relative to said plate to pivot said push member around said pivot rod; and
   a bias means coupled between the support and the rod to urge the rod to an upwardly extended position of the rod.

2. The liquid sampling apparatus of claim 1, further comprising a probe means for insertion into said test liquid and in communication with said cylinder.

3. A liquid sampling apparatus for drawing and/or expelling a test liquid of a predetermined amount into a hollow cylinder, comprising:
   a support;
   a vertically movable carriage;
   motive means mounted on said support to reciprocally move said carriage by a predetermined distance in a vertical direction relative to said support;
   a hollow cylinder fixed to said support with a longitudinal axis of said hollow cylinder being inclined at an acute angle to said vertical direction;
   a piston means movable in said cylinder to draw a liquid sample into or expel it from said cylinder;
   a rod having one end coupled to said piston means, the axis of said rod being parallel to the axis of said cylinder;
   a push member mounted on said carriage and positioned to engage the other end of said rod as said carriage is reciprocated vertially, said push member extending in a generally horizontal direction; and
   adjustment means for pivoting said push member to vary an angle between said push member and the horizontal direction, wherein said adjustment means comprises a plate connected at one end of the carriage and extending therefrom at a generally horizontal direction, a pivot rod connected at said one end of the plate and accommodated in a means defining an opening of said push member located at one end thereof, and a setting means at the other end of said plate for vertically moving the other end of said push member relative to said plate to pivot said push member around said pivot rod.

4. The liquid sampling apparatus of claim 3, wherein the push member and the other end of said rod are in abuttment with each other as the carriage is moved downward; and further comprising a bias means to urge the rod to an upwardly extended position.

* * * * *